(12) United States Patent
Ma

(10) Patent No.: US 10,290,247 B2
(45) Date of Patent: May 14, 2019

(54) LIGHTING JIG OF DISPLAY PANEL AND LIGHTING TEST METHOD

(71) Applicant: Wuhan China Star Optoelectronics Technology Co., Ltd., Wuhan, Hubei (CN)

(72) Inventor: Liang Ma, Guangdong (CN)

(73) Assignee: Wuhan China Star Optoelectronics Technology Co., Ltd, Wuhan, Hubei (CN)

( * ) Notice: Subject to any disclaimer, the term of this patent is extended or adjusted under 35 U.S.C. 154(b) by 18 days.

(21) Appl. No.: 15/533,458

(22) PCT Filed: May 12, 2017

(86) PCT No.: PCT/CN2017/084126
§ 371 (c)(1),
(2) Date: Jun. 6, 2017

(87) PCT Pub. No.: WO2018/192027
PCT Pub. Date: Oct. 25, 2018

(65) Prior Publication Data
US 2018/0308402 A1    Oct. 25, 2018

(51) Int. Cl.
*G01R 31/00* (2006.01)
*G09G 3/00* (2006.01)
(Continued)

(52) U.S. Cl.
CPC ........... *G09G 3/006* (2013.01); *G02F 1/1309* (2013.01); *G09G 3/3611* (2013.01); *G01N 2021/9513* (2013.01); *G09G 2300/0452* (2013.01)

(58) Field of Classification Search
CPC ....... G09G 3/006; G02F 1/1309; G02F 3/042; G02F 3/047; G02F 3/044;
(Continued)

(56) References Cited

U.S. PATENT DOCUMENTS

| 4,864,394 A | 9/1989 | Gillard |
| 2005/0052890 A1* | 3/2005 | Morita .................. G09G 3/3688 365/87 |

(Continued)

FOREIGN PATENT DOCUMENTS

| CN | 104715713 A | 6/2015 |
| CN | 106028560 A | 10/2016 |

(Continued)

*Primary Examiner* — Thang X Le
(74) *Attorney, Agent, or Firm* — Andrew C. Cheng

(57) ABSTRACT

The disclosure discloses a lighting jig of a display panel and a lighting test method. The lighting jig includes a signal generator configured to generate a plurality of control signals and a first digital signal, a controller connected with the signal generator and configured to light up subpixels corresponding to the control signals of corresponding rows in the display panel when an effective signal of the control signals and an effective signal of the first digital signal work simultaneously. The plurality of control signals are corresponding to the plurality of subpixels in each column of pixels respectively. In each period, temporal positions of the effective signal of the control signals corresponding to the subpixels required to be lit on and the effective signal of the first digital signal are identical. The sequence design of adopting special control signals and digital signals can prevent mischarging other subpixels during digital signal delay.

15 Claims, 3 Drawing Sheets

(51) Int. Cl.
*G02F 1/13* (2006.01)
*G09G 3/36* (2006.01)
*G01N 21/95* (2006.01)

(58) Field of Classification Search
CPC . G02F 2203/04103; G02F 2203/04112; G01R 31/2822; G01R 31/2825; G01R 31/3641
See application file for complete search history.

(56) References Cited

U.S. PATENT DOCUMENTS

| | | | | |
|---|---|---|---|---|
| 2005/0116919 | A1* | 6/2005 | Shin | G09G 3/325 345/100 |
| 2007/0046587 | A1* | 3/2007 | Takahara | G09G 3/3233 345/76 |
| 2009/0189924 | A1* | 7/2009 | Ogura | G09G 3/3233 345/690 |
| 2014/0354286 | A1* | 12/2014 | Kim | G09G 3/006 324/414 |
| 2016/0260367 | A1* | 9/2016 | Kwak | G09G 3/006 |
| 2016/0379906 | A1* | 12/2016 | Kim | G09G 3/3688 257/48 |

FOREIGN PATENT DOCUMENTS

| | | | |
|---|---|---|---|
| CN | 106057110 | A | 10/2016 |
| CN | 106057111 | A | 10/2016 |

\* cited by examiner

… (1) …

LIGHTING JIG OF DISPLAY PANEL AND LIGHTING TEST METHOD

FIELD OF THE DISCLOSURE

The disclosure relates to a display technical field, and more particularly to a lighting jig of a display panel and a lighting test method.

BACKGROUND

The development of display panels is more and more diverse, and requirements on mobile phones are more and more harsh. The most energy consuming section of the mobile phone is the screen, and a main aspect required to be considered by various panel manufacturers is to reduce energy consumption of the screen. The RGBW technique is adding a white (W) subpixel to the original RGB tricolor to become four-color pixel design. The design can enhance transmittance of the liquid crystal panel significantly. Energy consumption will be lower during displaying an image with the same brightness. Under the same energy consumption, the brightness is improved significantly, which stratifies the image better, and the image will be more clear.

The adoption of a WRGB panel yet has problems such as requirements on reducing flicker of panels and DC residue. The WRGB panel needs to be set up a certain display manner.

Under the certain display manner of the WRGB panel, some images are overloaded. At this point, mischarge and undercharge of the panel can be shown. Especially under the cell lighting of the WRGB panel, the procedure variation is relatively large, and resistance on metallic wires and jumpers increase, which can show mischarge and undercharge of the panel in certain images.

SUMMARY

The disclosure provides a lighting jig of a display panel and a lighting test method, which can prevent mischarging other subpixels during digital signal delay to affect effects of the lighting test.

To solve the technical problem above, the disclosure provides a lighting jig of a display panel, including a signal generator configured to generate a plurality of control signals and a first digital signal, a controller connected with the signal generator and configured to light up subpixels corresponding to the control signals of corresponding rows in the display panel when an effective signal of the control signals and an effective signal of the first digital signal work simultaneously. The plurality of control signals are corresponding to the plurality of subpixels in each column of pixels respectively. In each period, temporal positions of the effective signal of the control signals corresponding to the subpixels required to be lit on and the effective signal of the first digital signal are identical. The temporal position of the effective signal of the remaining control signals is situated at a distance of a set time slot from the effective signal of the first digital signal.

To solve the technical problem above, the disclosure further provides a lighting test method of a display panel, including inputting a gate signal into a gate signal input terminal of the display panel, inputting a plurality of control signals and a first digital signal into a controller to light up subpixels corresponding to the control signals of corresponding rows in the display panel when an effective signal of the control signals and an effective signal of the first digital signal work simultaneously. The plurality of control signals are corresponding to the plurality of subpixels in each column of pixels respectively. In each period, temporal positions of the effective signal of the control signals corresponding to the subpixels required to be lit on and the effective signal of the first digital signal are identical. The temporal position of the effective signal of the remaining control signals is situated at a distance of a set time slot from the effective signal of the first digital signal.

Distinguishing from the prior art, the lighting jig of the display panel provided by the disclosure includes a signal generator configured to generate a plurality of control signals and a first digital signal, a controller connected with the signal generator and configured to light up subpixels corresponding to the control signals of corresponding rows in the display panel when an effective signal of the control signals and an effective signal of the first digital signal work simultaneously. The plurality of control signals are corresponding to the plurality of subpixels in each column of pixels respectively. In each period, temporal positions of the effective signal of the control signals corresponding to the subpixels required to be lit on and the effective signal of the first digital signal are identical. The temporal position of the effective signal of the remaining control signals is situated at a distance of a set time slot from the effective signal of the first digital signal. By the manner above, the sequence design of adopting special control signals and digital signals can prevent mischarging other subpixels during digital signal delay to affect effects of the lighting test.

DETAILED DESCRIPTION OF PREFERRED EMBODIMENTS

Figure 1:
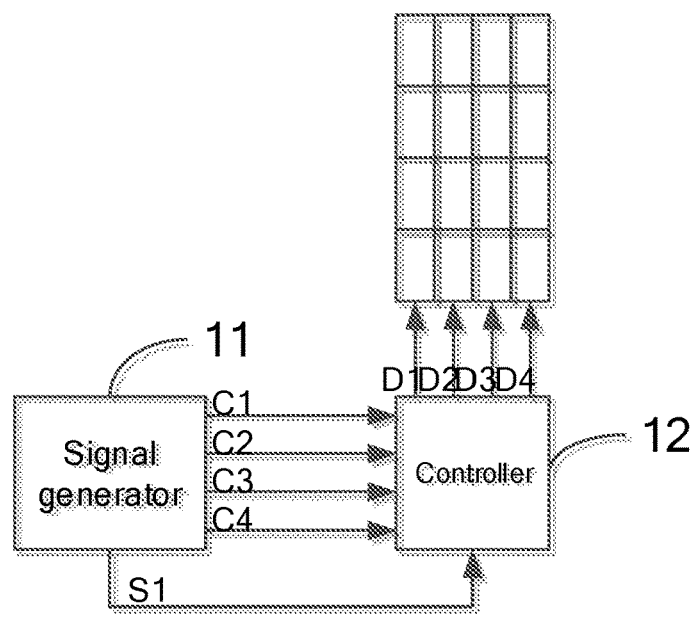
FIG. 1 is a structural schematic view of a lighting jig of a display panel according to an embodiment of the disclosure.

Referring to FIG. 1, FIG. 1 is a structural schematic view of a lighting jig of a display panel according to an embodiment of the disclosure. The lighting jig includes a signal generator 11 and a controller 12.

The signal generator 11 is configured to generate a plurality of control signals and a first digital signal.

In the embodiment, four paths of control signals are taken as an example. The four paths of control signals respectively are C1, C2, C3 and C4. The first digital signal is S1.

A controller 12 is connected with the signal generator 11, and is configured to light up subpixels corresponding to the control signals of corresponding rows in the display panel when an effective signal of the control signals and an effective signal of the first digital signal work simultaneously. The plurality of control signals are corresponding to the plurality of subpixels in each column of pixels respectively.

The effective signal of the control signals and the effective signal of the first digital signal working simultaneously indicates the control signals and the first digital signal can generate a digital signal to light up the corresponding subpixels. For instance, the effective signal of C1 and the effective signal of S1 work simultaneously to generate a D1 signal, which can light up the corresponding subpixels.

The control signals and the first digital signal will be illustrated by a specific example.

Figure 2:
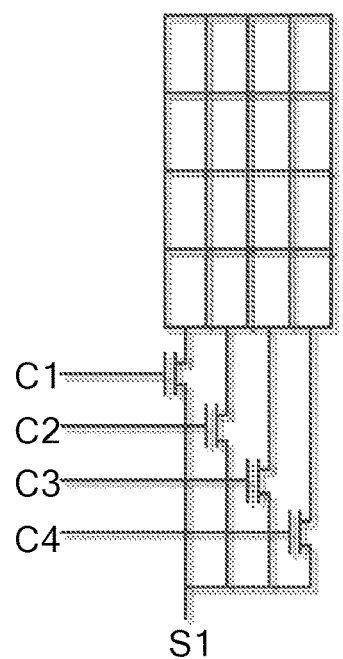
FIG. 2 is a specific structural schematic view of a controller in a lighting jig of a display panel according to an embodiment of the disclosure.

As shown in FIG. 2, the controller 12 includes a plurality of switch tubes. The control signals access gate electrodes of each of the switch tubes to control the switch tubes to be turned on or turned off. When the corresponding switch tubes are turned on, the first digital signal S1 can access the corresponding subpixels. Moreover, if the corresponding switch tubes are turned on and the first digital signal is the high level, the corresponding subpixels will be lit up.

Figure 3:
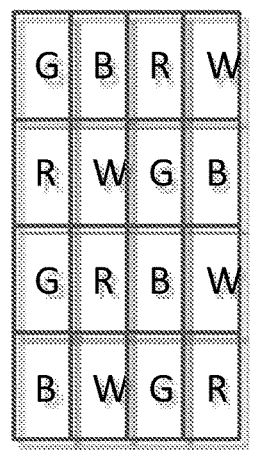
FIG. 3 is a schematic view of a subpixel arrangement in a lighting jig of a display panel according to an embodiment of the disclosure.

As shown in FIG. 3, FIG. 3 shows the arrangement of RGBW four-color pixels. Four subpixels in one row can be regarded as a pixel, or two adjacent subpixels in one row and two corresponding subpixels in the next row are regarded as a pixel, which will not be restricted. Moreover, the arrangement sequence of RGBW four colors can further be random. The sequence of the embodiment is merely an example.

It should be noted that the pixel arrangement shown in FIG. 3 is merely partial. 4 rows*4 columns of the subpixels form a pixel. A first row is G, B, R, W in sequence, a second row is R, W, G, B in sequence, a third row is G, R, B, W in sequence, a fourth row is B, W, G, R in sequence. And other pixels are identical to the pixel of 4 rows*4 columns.

Figure 4:
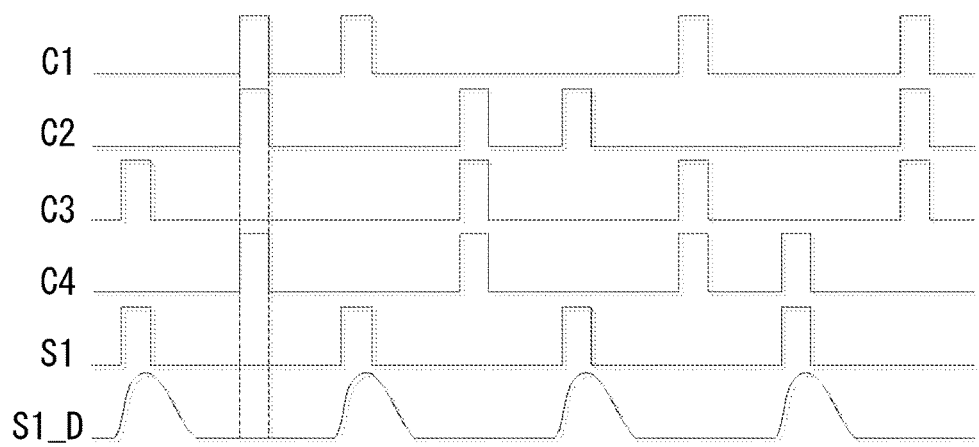
FIG. 4 is a sequence schematic view of a control signal and a digital signal in a lighting jig of a display panel according to an embodiment of the disclosure.

In the embodiment, the sequence manner of the control signals and the first digital signal is provided, as shown in FIG. 4.

The effective signal of each of the periods in the first digital signal S1 is located at an identical temporal position in each period duration. In each period, temporal positions of the effective signal of the control signals corresponding to the subpixels required to be lit on and the effective signal of the first digital signal being identical, the temporal position of the effective signal of the remaining control signals situated at a distance of a set time slot from the effective signal of the first digital signal.

The embodiment will be illustrated in detail with reference to FIG. 3 and FIG. 4.

In the first period, the R subpixels in the first row are lit up. As the R subpixel is the third, the high level of C3 and the high level of S1 are corresponding, which light up the R subpixels in the first row. Moreover, as the high level time of C1, C2 and C4 is later than C3, S1 will not be charged when the first subpixel, the second subpixel and the fourth subpixel are turned on, even though S1 is delayed.

In the second period, the R subpixels in the second row are lit up. As the R subpixel is the first, the high level of C1 and the high level of S1 are corresponding, which light up the R subpixels in the second row. Moreover, as the high level time of C2, C3 and C4 is later than C1, S1 will not be charged when the second subpixel, the third subpixel and the fourth subpixel are turned on, even though S1 is delayed.

In the third period, the R subpixels in the third row are lit up. As the R subpixel is the second, the high level of C2 and the high level of S1 are corresponding, which light up the R subpixels in the third row. Moreover, as the high level time of C1, C3 and C4 is later than C2, S1 will not be charged when the first subpixel, the third subpixel and the fourth subpixel are turned on, even though S1 is delayed.

In the fourth period, the R subpixels in the fourth row are lit up. As the R subpixel is the fourth, the high level of C4 and the high level of S1 are corresponding, which light up the R subpixels in the fourth row. Moreover, as the high level time of C1, C2 and C3 is later than C4, S1 will not be charged when the first subpixel, the second subpixel and the third subpixel are turned on, even though S1 is delayed.

Optionally, the effective signal of each of the periods in the first digital signal is located at an identical temporal position in each period duration. For instance, the first digital signal can provide a high level signal of a duration in the initial phase of each of the periods. In other embodiments, the high level signal can be provided at other temporal positions in the period.

Optionally, the delayed set time can be set up according to the extent of the delay of the first digital signal S1. The control signals corresponding to the unlit subpixels should be guaranteed not to be the high level when the first digital signal S1 is delayed. For instance, the set time slot is longer than the duration of the effective signal in the first digital signal.

By the manner above, the sequence design of adopting special control signals and digital signals can prevent mischarging other subpixels during digital signal delay to affect effects of the lighting test.

Figure 5:
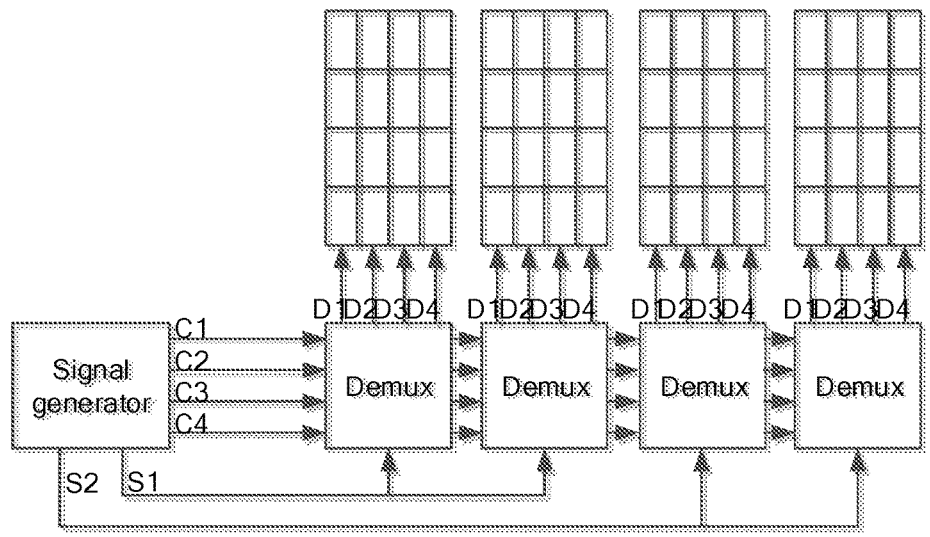
FIG. 5 is a structural schematic view of a lighting jig of a display panel according to another embodiment of the disclosure.

Referring to FIG. 5, FIG. 5 is a structural schematic view of a lighting jig of a display panel according to another embodiment of the disclosure.

The controller includes a plurality of demuxs. Each of the demuxs is configured to receive N paths of control signals and the first digital signal to light up the subpixels corresponding to the control signals in N columns of the subpixels of corresponding rows in the display panel. N is a positive integer.

For instance, the demux provided by the embodiment is four paths. One demux is configured to provide the digital signal to four columns of subpixels.

It can be understood that according to the combination of embodiments of FIG. 3 and FIG. 4 above, when the digital signals are the same, in the first period, R subpixels of each of the pixels in the first row will be lit up. As the R subpixel is the third one of each of the pixels, the high level of C3 and the high level of S1 are corresponding, which light up all the R subpixels in the first row. Moreover, as the high level time of C1, C2 and C4 is later than C3, S1 will not be charged when the first subpixel, the second subpixel and the fourth subpixel are turned on, even though S1 is delayed.

Optionally, as shown in FIG. 5, in another embodiment, the signal generator generates two digital signals with opposite waveforms, which are the first digital signal S1 and the second digital signal S2. The controller is further configured to select one of the first digital signal and the second digital signal to be a digital signal for lighting up the subpixels.

For instance, half of the subpixels in the display panel can be lit up by the first digital signal, and the other half of the subpixels can be lit up by the second digital signal. For instance, the number of demuxs is 100. The first digital signal can access to 50 demuxs on the left, and the second digital signal can access to 50 demuxs on the right.

Figure 6:
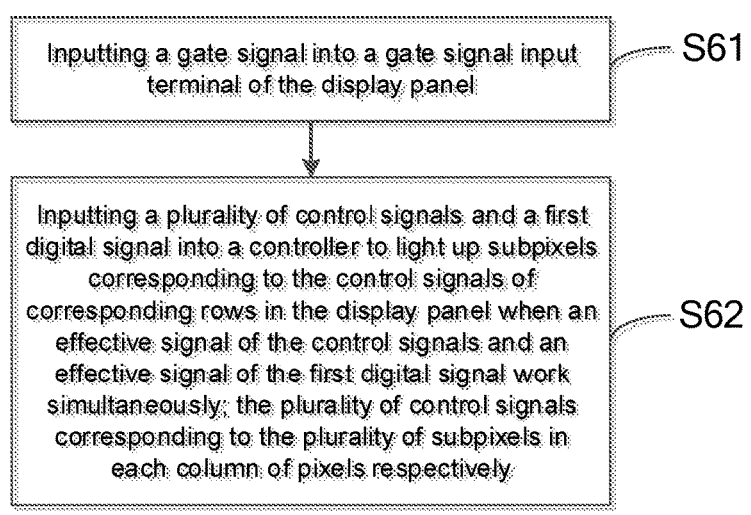
FIG. 6 is a flowchart of a lighting test method of a display panel according to an embodiment of the disclosure.

FIG. 6, FIG. 6 is a flowchart of a lighting test method of a display panel according to an embodiment of the disclosure. The method includes:

S61, inputting a gate signal into a gate signal input terminal of the display panel.

S62, inputting a plurality of control signals and a first digital signal into a controller to light up subpixels corresponding to the control signals of corresponding rows in the display panel when an effective signal of the control signals and an effective signal of the first digital signal work simultaneously. The plurality of control signals are corresponding to the plurality of subpixels in each column of pixels respectively.

It can be understood that the lighting test and the display principle of the display panel are similar. The gate electrode can still follow the conventional manner such as progressive scanning, interlace scanning, forward and reverse scanning, etc., merely the digital signals accessed from the digital signal input terminal are substituted for the digital signals provided in the embodiment (e.g. the first digital signal S1 or the second digital signal S2).

In each period, temporal positions of the effective signal of the control signals corresponding to the subpixels required to be lit on and the effective signal of the first digital signal are identical. The temporal position of the effective signal of the remaining control signals is situated at a distance of a set time slot from the effective signal of the first digital signal.

The lighting test method of the display panel provided by the embodiment and the principle of the light jig in the previous embodiment are similar, which will not be repeated.

The description above is merely embodiments of the disclosure, which cannot limit the protection scope of the disclosure. Any equivalent structure or process according to contents of the disclosure and the figures, or direct or indirect application in other related fields should be included in the protected scope of the disclosure.

What is claimed is:

1. A lighting jig of a display panel, comprising:
   a signal generator configured to generate a plurality of control signals and a first digital signal;
   a controller connected with the signal generator and configured to light up subpixels corresponding to the control signals of corresponding rows in the display panel when an effective signal of the control signals and an effective signal of the first digital signal work simultaneously; the plurality of control signals corresponding to the plurality of subpixels in each column of pixels respectively;
   in each period, temporal positions of the effective signal of the control signals corresponding to the subpixels required to be lit on and the effective signal of the first digital signal being identical, the temporal position of the effective signal of the remaining control signals situated at a distance of a set time slot from the effective signal of the first digital signal;
   the effective signal of each of the periods in the first digital signal located at an identical temporal position in each period duration, the effective signal being a high level signal;
   wherein the signal generator is further configured to generate a second digital signal;
   the controller is further configured to select one of the first digital signal and the second digital signal to be a digital signal for lighting up the subpixels; waveforms of the first digital signal and the second digital signal are opposite.

2. The lighting jig according to claim 1, wherein the controller comprises a plurality of demuxs, each of the demuxs is configured to receive N paths of control signals and the first digital signal to light up the subpixels corresponding to the control signals in N columns of the subpixels of corresponding rows in the display panel; N is a positive integer.

3. The lighting jig according to claim 2, wherein the display panel is an RGBW four-color display panel, the demuxes are configured to receive four paths of control signals and the first digital signal to light up the subpixels corresponding to the control signals in four columns of subpixels of corresponding rows in the display panel.

4. The lighting jig according to claim 3, wherein 4 rows*4 columns of the subpixels form a pixel, a first row is G, B, R, W in sequence, a second row is R, W, G, B in sequence, a third row is G, R, B, W in sequence, a fourth row is B, W, G, R in sequence.

5. The lighting jig according to claim 1, wherein the controller is further configured to adopt the first digital signal to light up half of the subpixels in the display panel, and adopt the second digital signal to light up the other half of the subpixels in the display panel.

6. The lighting jig according to claim 1, wherein the set time slot is longer than the duration of the effective signal in the first digital signal.

7. A lighting jig of a display panel, comprising:
   a signal generator configured to generate a plurality of control signals and a first digital signal;
   a controller connected with the signal generator and configured to light up subpixels corresponding to the control signals of corresponding rows in the display panel when an effective signal of the control signals and an effective signal of the first digital signal work simultaneously; the plurality of control signals corresponding to the plurality of subpixels in each column of pixels respectively;
   in each period, temporal positions of the effective signal of the control signals corresponding to the subpixels required to be lit on and the effective signal of the first digital signal being identical, the temporal position of the effective signal of the remaining control signals situated at a distance of a set time slot from the effective signal of the first digital signal;
   wherein the signal generator is further configured to generate a second digital signal;
   the controller is further configured to select one of the first digital signal and the second digital signal to be a digital signal for lighting up the subpixels; waveforms of the first digital signal and the second digital signal are opposite.

8. The lighting jig according to claim 7, wherein the controller comprises a plurality of demuxs, each of the demuxs is configured to receive N paths of control signals and the first digital signal to light up the subpixels corresponding to the control signals in N columns of subpixels of corresponding rows in the display panel; N is a positive integer.

9. The lighting jig according to claim 8, wherein the display panel is an RGBW four-color display panel, the demuxs are configured to receive four paths of control signals and the first digital signal to light up the subpixels corresponding to the control signals in four columns of subpixels of corresponding rows in the display panel.

10. The lighting jig according to claim 9, wherein 4 rows*4 columns of the subpixels form a pixel, a first row is G, B, R, W in sequence, a second row is R, W, G, B in sequence, a third row is G, R, B, W in sequence, a fourth row is B, W, G, R in sequence.

11. The lighting jig according to claim 7, wherein the controller is further configured to adopt the first digital signal to light up half of the subpixels in the display panel, and adopt the second digital signal to light up the other half of the subpixels in the display panel.

12. The lighting jig according to claim 7, wherein the effective signal is a high level signal.

13. The lighting jig according to claim 7, wherein the effective signal of each of the periods in the first digital signal is located at an identical temporal position in each period duration.

14. The lighting jig according to claim 7, wherein the set time slot is longer than the duration of the effective signal in the first digital signal.

15. A lighting test method of a display panel, comprising:
inputting a gate signal into a gate signal input terminal of the display panel;
inputting a plurality of control signals, a first digital signal and a second digital signal into a controller, such that the controller selects one of the first digital signal and the second digital signal to light up subpixels corresponding to the control signals of corresponding rows in the display panel when an effective signal of the control signals and an effective signal of the first digital signal work simultaneously; the plurality of control signals corresponding to the plurality of subpixels in each column of pixels respectively, wherein waveforms of the first digital signal and the second digital signal are opposite;
in each period, temporal positions of the effective signal of the control signals corresponding to the subpixels required to be lit on and the effective signal of the first digital signal being identical, the temporal position of the effective signal of the remaining control signals situated at a distance of a set time slot from the effective signal of the first digital signal.

* * * * *